US009618522B2

(12) United States Patent
Hu

(10) Patent No.: US 9,618,522 B2
(45) Date of Patent: Apr. 11, 2017

(54) DIAGNOSTIC TESTING IN DEMENTIA AND METHODS RELATED THERETO

(71) Applicant: EMORY UNIVERSITY, Atlanta, GA (US)

(72) Inventor: William T. Hu, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 14/417,672

(22) PCT Filed: Sep. 5, 2013

(86) PCT No.: PCT/US2013/058177
§ 371 (c)(1),
(2) Date: Jan. 27, 2015

(87) PCT Pub. No.: WO2014/039630
PCT Pub. Date: Mar. 13, 2014

(65) Prior Publication Data
US 2016/0146837 A1    May 26, 2016

Related U.S. Application Data

(60) Provisional application No. 61/696,909, filed on Sep. 5, 2012.

(51) Int. Cl.
*G01N 33/68*    (2006.01)
*C12Q 1/68*    (2006.01)

(52) U.S. Cl.
CPC ....... *G01N 33/6896* (2013.01); *C12Q 1/6883* (2013.01); *C12Q 2600/156* (2013.01); *G01N 2440/14* (2013.01); *G01N 2800/2814* (2013.01); *G01N 2800/2821* (2013.01)

(58) Field of Classification Search
None
See application file for complete search history.

(56) References Cited

U.S. PATENT DOCUMENTS

| | | | |
|---|---|---|---|
| 6,680,173 B2 | 1/2004 | Vanmechelen | |
| 7,387,879 B2 | 6/2008 | Vanmechelen | |
| 2012/0083761 A1* | 4/2012 | Malecki | A61K 41/0038 604/500 |
| 2012/0100545 A1* | 4/2012 | Inoue | C12Q 1/689 435/6.11 |
| 2012/0190672 A1* | 7/2012 | Hall | C07D 513/04 514/224.2 |

FOREIGN PATENT DOCUMENTS

| WO | 0155725 | 8/2001 |
|---|---|---|
| WO | 2009044119 | 4/2009 |
| WO | 2011005628 | 1/2011 |

OTHER PUBLICATIONS

Alberici 2004 "frontotemproal dementia: impact of p301L tau mutation on a healthy carrier" J neurol neurosurg psychiatry 75:1607-1610.*
Boban 2010 "csf tau proteins in differential diagnosis of dementia" translational neurosciences 1(1):43-48.*
Hu 2010 "novel csf biomarkers for alzheimer's disease and mild cognitive impairment" acta neuropathol 119(6):669-678.*
Hu 2011 "biomarkers in frontotemporal lobar degenerations—progress and challenges" progress in neurobiology 95:636-648.*
Lewczuk 2004 "tau protein phosphorylated at threonine 181 in csf as a neurochemical biomarker in alzheimer's disease" J mol neurosci 23:115-122.*
Rosso 2003 "total tau and phosphorylated tau 181 levels in the cerebrospinal fluid of patients with frontotemporal dementia due to p301L and g272v tau mutations" arch neurol 60:1209-1213.*
Schonknecht 2003 "levels of total tau and tau protein phosphorylated at threonine 181 in patients with incipient and manifest alzheimer's disease" neurosci letters 339:172-174.*
Schoonenboom 2011 "cerebrospinal fluid markers for differential dementia diagnosis in a large memory clinic cohort" neurology 78: 47-54.*
Sjogren 2001 "both total and phosphorylated tau are increased in alzheimer's disease" j neurol neurosurg psychiat 70:624-630.*
Vanmechelen 2000 "quantification of tau phosphorylated at threonine 181 in human cerebrospinal fluid: a sandwich ELISA with a synthetic phosphopeptide for standardization" neurosci letters 285:49-52.*
USCAFC (2014) "Myriad Genetics v Ambry".*
Bloomberg BNA (2015) "Ameritox v Millennium".*
USCAFC (2015) "Ariosa v Sequenom".*
Grossman et al. Cerebrospinal fluid profile in frontotemporal dementia and Alzheimer's disease, Ann Neurology, Annals of Neurology, 2005, 57(5): 721-729.
Hu et al. Novel CSF biomarkers for frontotemporal lobar degenerations, Neurology, 2010, 75(23): 2079-2086.
Hu et al. Reduced CSF p-T au 181 to Tau ratio is a biomarker for FTLD-TDP, Neurology, 2013; 81: 1945-1952.
Kuiperij et al. Tau Rather than TDP-43 Proteins are Potential Cerebrospinal Fluid Biomarkers for Frontotemporal Lobar Degeneration Subtypes: A Pilot Study, J Alzheimers Dis. 2016.
Riemenschneider et at. Phospho-tau/total tau ratio in cerebrospinal fluid discriminates Creutzfeldt-Jakob disease from other dementias, Mol Psychiatry. 2003, 8(3): 343-7.
Thomann et al. Association of total tau and phosphorylated tau 181 protein levels in cerebrospinal fluid with cerebral atrophy in mild cognitive impairment and Alzheimer disease, J Psychiatry Neurosci 2009;34(2):136-42.
Extended European search report issued for EP Application No. 13835342.0 dated Apr. 15, 2016.

* cited by examiner

*Primary Examiner* — Adam M Weidner
(74) *Attorney, Agent, or Firm* — Emory Patent Group

(57) ABSTRACT

This disclosure relates to diagnostic testing for subjects with or at risk of dementia and methods related thereto. In certain embodiments, the disclosure relates to methods of diagnosing a frontotemporal lobar degeneration subtype comprising measuring total Tau and Tau phosphorylated at threonine 181 in a sample from a subject, calculating a ratio of Tau phosphorylated at threonine 181 to total Tau, and making a diagnosis of the subtype based on said ratios. Typically, the sample is of cerebrospinal fluid and the frontotemporal lobar degeneration subtypes are selected from frontotemporal lobar degeneration with immunoreactive lesions to Tau and frontotemporal lobar degeneration with immunoreactive lesions to TAR DNA binding protein of 43 kD.

10 Claims, 8 Drawing Sheets

DIAGNOSTIC TESTING IN DEMENTIA AND METHODS RELATED THERETO

CROSS REFERENCE TO RELATED APPLICATIONS

This application is the National Stage of International Application Number PCT/US2013/058177 filed Sep. 5, 2013, which claims the benefit of priority to U.S. Provisional Application No. 61/696,909 filed Sep. 5, 2012. The entirety of each of these applications is hereby incorporated by reference for all purposes.

FIELD

This disclosure relates to diagnostic testing for subjects with or at risk or dementia and methods related thereto.

BACKGROUND

Frontotemporal dementia (FTD) is a common cause of dementia in people under the age of 65 years. Pathologic causes of FTLD may be categorized according to the main pathologic inclusion protein, and the majority of FTLD cases are either FTLD with inclusions immunoreactive to TAR DNA binding protein of 43 kD (FTLD-TDP) or FTLD with inclusions immunoreactive to Tau (FTLD-Tau). The clinical prediction of underlying FTLD pathology based on clinical features, neuropsychological testing, or imaging patterns has been less than optimal, especially in patients with prominent behavioral changes who represent the largest FTLD syndromic group. The poor prediction of underlying FTLD pathology has also significantly hindered the progress in clinical trial design in FTLD, as therapies targeting TDP or Tau cannot be reliably given to patients with the corresponding pathology. Thus, there is a need to improve diagnosis of FTLD subtypes.

Cerebrospinal fluid (CSF) levels of total-tau and phosphorylated-tau have been assessed for certain neurodegenerative diseases. See Grossman et al., Annals of Neurology, 2005, 57(5):721-729. See also Hu et al., Neurology, 2010, 75(23):2079-2086 and Riemenschneider et al., Mol Psychiatry., 2003, 8(3):343-7. An association of total tau and phosphorylated tau 181 protein levels in cerebrospinal fluid has been reported with cerebral atrophy in mild cognitive impairment and Alzheimer disease. See Thomann et al., J Psychiatry Neurosci., 2009, 34(2):136-142. The differential diagnosis of a tauopathy versus a non-tauopathy based on the detection of the ratio of phospho-tau (181)/total tau is reported in U.S. Pat. Nos. 6,680,173 and 7,387,879.

SUMMARY

This disclosure relates to diagnostic testing for subjects with or at risk of dementia and methods related thereto. In certain embodiments, the disclosure relates to methods of diagnosing a frontotemporal lobar degeneration subtype comprising measuring total Tau and Tau phosphorylated at threonine 181 in a sample from a subject, calculating a ratio of Tau phosphorylated at threonine 181 to total Tau, and making a diagnosis of the subtype based on said ratios. Typically, the sample is of cerebrospinal fluid and the frontotemporal lobar degeneration subtypes are selected from frontotemporal lobar degeneration with immunoreactive lesions to Tau and frontotemporal lobar degeneration with immunoreactive lesions to TAR DNA binding protein of 43 kD.

In some embodiments, the methods initially comprise the step of measuring beta-amyloid 1-42 and making a diagnosis of Alzheimer's disease or a frontotemporal lobar degeneration subtype. Typically, subjects have total Tau to beta-amyloid 1-42 ratio of less than 0.3. In some embodiments, subjects do not have total Tau to beta-amyloid 1-42 ratio of about or greater than 0.3.

In some embodiments, a decreased relative phosphorylation of Tau at threonine 181 when compared to levels typical of a subject of normal cognition indicates the subject has frontotemporal lobar degeneration subtype with immunoreactive lesions to TAR DNA binding protein of 43 kD or ALS. In some embodiments, a phosphorylation of Tau at threonine 181 to total Tau ratio of less than about 0.3 indicates the subject has frontotemporal lobar degeneration subtype with immunoreactive lesions to TAR DNA binding protein of 43 kD. In some embodiments, a phosphorylation of Tau at threonine 181 to total Tau ratio of greater than about 0.3 indicates the subject has frontotemporal lobar degeneration with immunoreactive lesions to Tau.

In some embodiments, the subject is diagnosed with a mutation associated with a frontotemporal lobar degeneration associated disease or condition, e.g., C9ORF72, PGRN, or MAPT mutation. In some embodiments, the subject exhibits symptoms of progressive behavior or language difficulties.

In some embodiments, the methods further comprise the step of recording the measurements or ratios. In some embodiments, the measurements are recorded in an electronic format. In some embodiments, the methods further comprise the step of recording the diagnosis. In some embodiments, the methods further comprise the step of reporting the measurements, ratios, or diagnosis to a medical professional, the subject, or representative thereof.

In some embodiments, the disclosure relates to a method of preparing a CSF sample for analysis of a component comprising one or more, all, or a combination of the following steps: obtaining a CSF sample; freezing the sample; thawing the sample; warming the sample to about or above 30, 35, or 37 degree Celsius; vortexing the sample for about or more than 5, 10, 15 seconds; vortexing the sample for about or more than 5, 10, 15 seconds more than once; and measuring the amount of beta-amyloid 1-42, total Tau, and/or Tau phosphorylated at threonine 181 in the sample.

In some embodiments, the disclosure relates to a method of preparing a CSF sample for analysis of a component comprising the following steps: obtaining a CSF sample; freezing the sample; thawing the sample; vortexing the sample for about or more than 5, 10, 15 seconds; and vortexing the sample for about or more than 5, 10, 15 seconds for a second time; and measuring the amount of beta-amyloid 1-42, total Tau, and/or Tau phosphorylated at threonine 181 in the sample.

In some embodiments, the disclosure relates to methods disclosed herein further comprising the step of preparing a CSF sample for analysis of a component comprising one or more, all, or a combination of the following steps: obtaining a CSF sample; freezing the sample; thawing the sample; warming the sample to about or above 30, 35, or 37 degree Celsius; vortexing the sample for about or more than 5, 10, 15 seconds; vortexing the sample for about or more than 5, 10, 15 seconds more than once; and measuring the amount of beta-amyloid 1-42, total Tau, and/or Tau phosphorylated at threonine 181 in the sample.

DETAILED DISCUSSION

Figure 1:
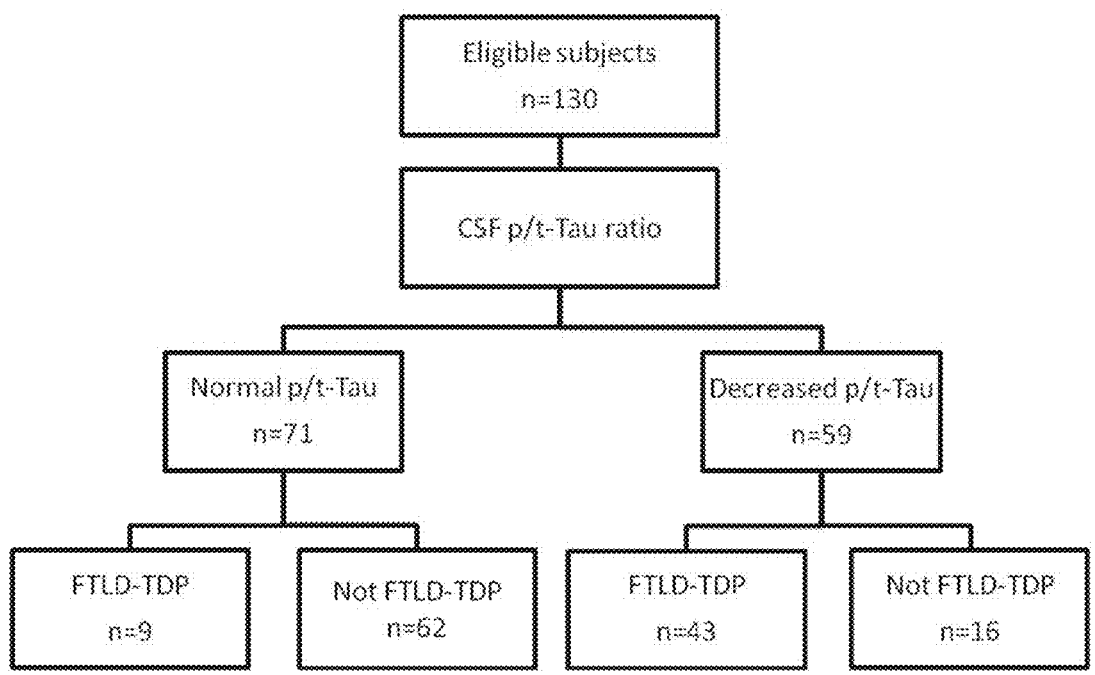
FIG. 1 shows data on the clinicopathologic diagnosis of subjects according to CSF p/t-Tau ratio. The first validation cohort (n=30) contained 10 subjects (3 with FTLD-TDP) with normal p/t-Tau and 20 subjects (16 with FTLD-TDP) with decreased p/t-Tau, and the second validation cohort (n=100) contained 61 subjects (6 with FTLD-TDP) with normal p/t-Tau and 39 subjects (27 with FTLD-TDP) with decreased p/t-Tau.
Figure 2A:
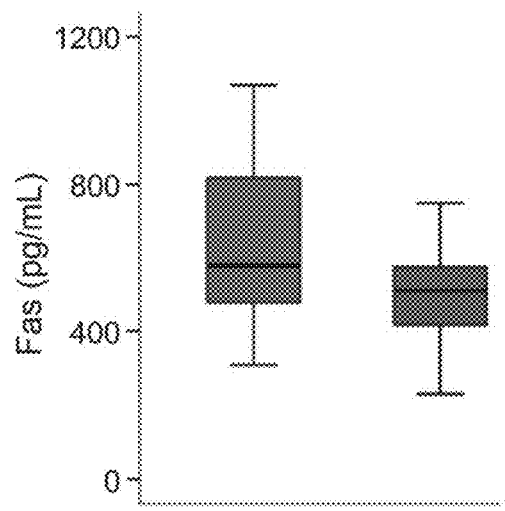
FIG. 2A shows data on CSF biomarkers levels in FTLD-TDP and FTLD-Tau. Levels of Fas in Validation Cohort 1 from Emory between FTLD-TDP and FTLD-Tau.
Figure 2B:
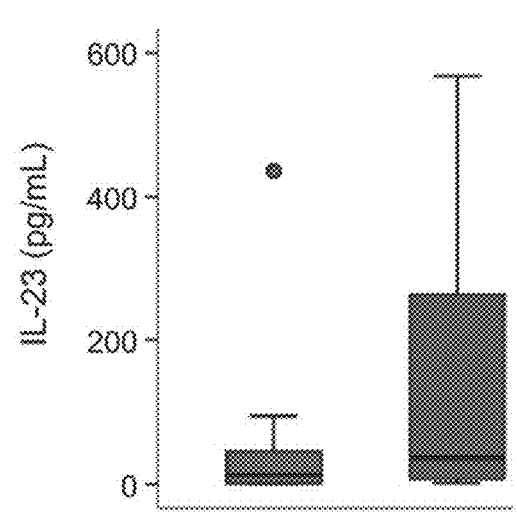
FIG. 2B shows levels of IL-23.
Figure 2C:
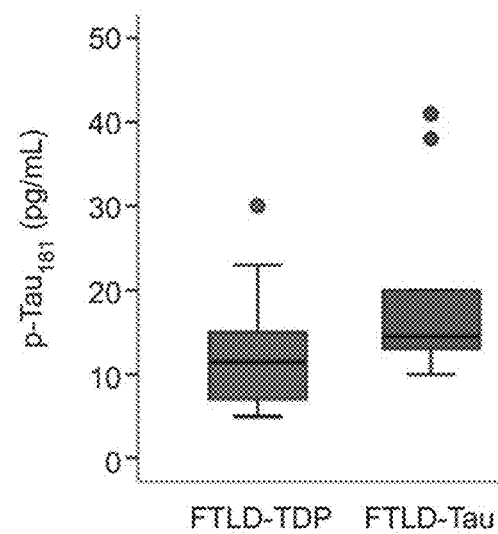
FIG. 2C shows levels of p-Tau181.
Figure 2D:
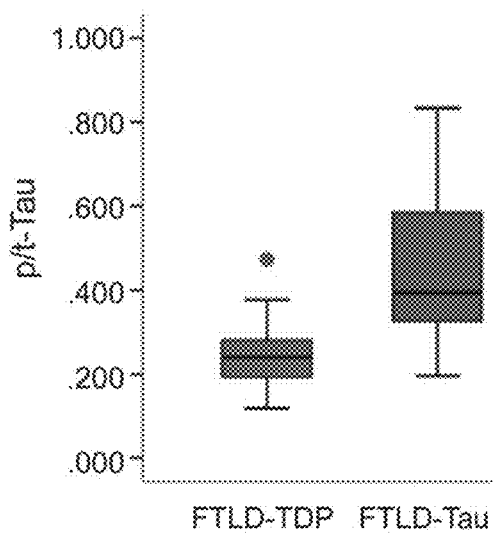
FIG. 2D shows p/t-Tau ratio.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise.

In this specification and in the claims that follow, reference will be made to a number of terms that shall be defined to have the following meanings unless a contrary intention is apparent.

Prior to describing the various embodiments, the following definitions are provided and should be used unless otherwise indicated.

"Sample" or "biological sample" means biological material isolated from a subject. The biological sample may contain any biological material suitable for detecting the desired biomarkers, and may comprise cellular and/or non-cellular material from the subject. The sample can be isolated from any suitable biological tissue or fluid such as, for example, prostate tissue, blood, blood plasma, urine, or cerebral spinal fluid (CSF).

"Subject" means any animal, but is preferably a mammal, such as, for example, a human, monkey, mouse, or rabbit.

A biochemical biomarker in cerebrospinal fluid (CSF) or blood enhances a clinician's ability to identify underlying FTLD pathology early in the disease course and the logical design of therapeutic trials targeting TDP and Tau. Clinical syndromes associated with frontotemporal lobar degenerations (FTLD) are poor predictors of underlying pathology in most cases. A reliable biomarker that can predict the exact FTLD pathology will not only markedly enhance the early diagnosis of FTLD subtypes, but also accelerate the development of substrate-specific therapies targeting the FTLD pathologic subtypes. Using cases of FTLD with known pathologic subtypes including patients with mutations and FTLD-plus disorders, total Tau (t-Tau) and Tau phosphorylated at threonine 181 (p-Tau181) were identified to be different between the two main FTLD subtypes, FTLD with immunoreactive lesions to TDP-43 (FTLD-TDP) and those with immunoreactive lesions to Tau (FTLD-Tau). In a training cohort of 23 patients, decreased p-Tau181/t-Tau ratio predicted FTLD-TDP with 93% sensitivity and 78% specificity. These findings were replicated in patients independently with known pathology. Patients with high likelihood FTLD-TDP pathology including those with semantic variant primary progressive aphasia and amyotrophic lateral sclerosis without dementia. The CSF p-Tau181/t-Tau ratio can be used in the early diagnosis of FTLD-TDP or ALs, and can be used in conjunction with CSF beta-amyloid 1-42 levels in the differential diagnosis of Alzheimer's disease, FTLD-TDP, and FTLD-Tau.

Tau Proteins and Neurodegenerative Disorders

Tau proteins are more abundant in neurons of the central nervous system and typically expressed at low levels in CNS cells. Defective tau proteins result in dementias such as Alzheimer's disease. The tau proteins are the product of alternative splicing from the human MAPT (microtubule-associated protein tau) gene. The MAPT gene for encoding tau protein is located on chromosome 17q21, containing 16 exons. Tau proteins interact with tubulin to promote tubulin assembly into microtubules. Tau isoforms are distinguished by their number of binding domains. Isoforms have three or four binding domains located in the carboxy-terminus. Kinases and phosphatases too play a role in regulating the phosphorylation of tau. Hyperphosphorylation of the tau protein (tau inclusions, pTau) can result in the self-assembly of tangles of paired helical filaments and straight filaments, which are involved in the pathogenesis of Alzheimer's disease and other tauopathies.

Frontotemporal lobar degeneration (FTLD) refers to disorders associated with atrophy in the frontal lobe or temporal lobe of the brain resulting in dementia other than those with Alzheimer's disease. FTLD may coexist with other neurodegenerative disorders such as Progressive Supranuclear Palsy (PSP) and Amyotrophic lateral sclerosis (ALS). Mutations in the gene encoding the microtubule-associated protein tau (MAPT) were shown to cause familial FTLD with parkinsonism linked to chromosome 17q21 (FTDP-17). The patients typically show neurofibrillary inclusions composed of hyperphosphorylated tau (FTLD-tau).

Many FTLD patients lack mutations in MAPT and typically fail to show tau-positive inclusions. In contrast, these patients typically have ubiquitin(ub)-positive inclusions and TDP-43 positive immunohistochemistry, thus FTLD-TDP is a FTLD subtype. FTLD-TDP subtype is sometimes linked to mutations in progranulin (PGRN). Post-mortem immunohistological staining of brain tissue is typically used to differentiate FTLD-TDP from FTLD-Tau in deceased patients. Prior to the current disclosure diagnosis of living subjects with FTLD-TDP or FTLD-Tau subtypes was challenging.

Amyotrophic lateral sclerosis (ALS) is sometimes referred to as motor neuron disease. Abnormal accumulation of TDP-43 is a key feature in ALS, and makes ALS part of the FTLD-TDP spectrum of disorders. There are known hereditary factors in familial ALS (FALS). An expanded hexanucleotide repeat is in C9ORF72 is associated with ALS combined with frontotemporal dementia ALS-FTD. Superoxide dismutase (SOD1) mutations are associated with a portion of familial cases of ALS. A common ALS-causing SOD1 mutation in North American patients is A4V.

Progressive Supranuclear Palsy (PSP) typically refers to a subject with an accumulation of tau protein and neuropil threads. Similar histopathological findings, however, can be seen in patients with other neurodegenerative diseases such as Alzheimer's, and Postencephalitic Parkinsonism (PEP). However, the predominant accumulation of Tau protein is key feature of PSP, and makes PSP part of the FTLD-Tau spectrum of disorders. Another significant feature of PSP pathology is astrocytic tufts and neurofibrillary tangles that show tau-positive immunohistochemistry.

"Total Tau" refers to the human Tau protein regardless of phosphorylation state in a sample. Many commercial assays are available for use in the detection of total Tau and phosphorylated Tau from cerebral spinal fluid (CSF) such as those reported in U.S. Pat. Nos. 6,680,173 and 7,387,879, both hereby incorporated by reference in their entirety. In a typical assay, a monoclonal capture antibody specific for human Tau has been coated onto a solid surface, such as a microplate, for incubation with a sample. Standards of known Tau content may be used for side-by-side comparisons. The Tau protein binds to the immobilized (capture) antibody. After washing the surface, a second antibody specific for Tau is mixed in. During the second incubation, this antibody serves as a detection antibody by binding to the immobilized Tau protein. The second antibody may or may not contain a conjugated dye, quantum dot or other marker. In some instances a horseradish peroxidase-labeled anti-IgG is added. This binds to the detection antibody. A substrate solution (TMB) is mix with the surface to act upon by the horseradish peroxidase to produce color. The intensity of this colored product is proportional and correlates to the concentration of human Tau present in the sample, and e.g., the optical density can be read on a microplate reader.

Cerebrospinal Fluid (CSF) Tau Phosphorylation Distinguishes Between FTLD-TDP and FTLD-Tau Frontotemporal lobar degeneration (FTLD) is distinct from Alzheimer's disease (AD) and Parkinson's disease in that there is poor correlation between the clinical syndromes (such as behavioral variant frontotemporal degeneration, bv-FTD) and the specific underlying pathology. While some syndromes have better association with FTLD-TDP or FTLD-Tau, it is difficult to use group-level associations to predict each individual's exact pathology. A reliable biomarker which accurately predicts the underlying FTLD pathology at the patient level is desperately needed for successful implementation of substrate specific therapeutic trials targeting abnormal TDP-43 or Tau accumulations. Patients were selected with known FTLD-TDP pathology (autopsy, mutations associated with FTLD-TDP, and FTD with amyotrophic lateral sclerosis [ALS] or FTD-ALS) and FTLD-Tau pathology (autopsy, mutations associated with FTLD-Tau, and FTD with progressive supranuclear palsy [PSP] or FTD-PSP) from University of Pennsylvania (Penn)

to identify novel ante-mortem CSF FTLD biomarkers. Using a commercial platform, levels of 10 CSF proteins and peptides were found to differ between FTLD-TDP and FTLD-Tau, with a panel of five proteins distinguishing FTLD-TDP cases from FTLD-Tau cases with 84% diagnostic accuracy. To validate these five biomarkers, FTLD subjects were recruited to undergo CSF collection at Emory University (Emory), and set up independent assays to measure the putative CSF biomarkers as well as levels of total Tau (t-Tau) and Tau phosphorylated at threonine 181 (p-Tau181). The most promising biomarker or biomarker panel was then analyzed in a separate validation cohort from Emory and Penn to determine its sensitivity and specificity for FTLD-TDP.

Figure 3A:
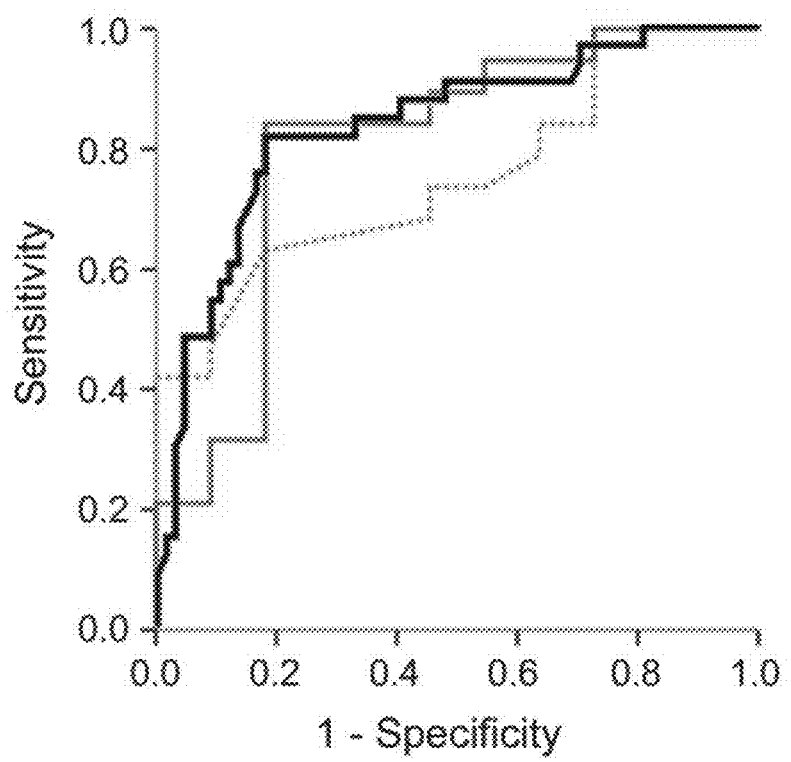
FIG. 3A shows data on the diagnostic performance of Tau-related biomarkers in identifying FTLD-TDP. ROC curve analysis of CSF p-Tau181 levels (gray dashed line) and CSF p/t-Tau ratio (blue solid line) in Validation Cohort 1, and the CSF p/t-Tau ratio (black solid line) in Validation Cohort 2.

It was desired to validate putative CSF biomarkers of FTLD subtypes in a single center Validation Cohort 1 (n=30) or a two-centered Validation Cohort 2 (n=100, Table 1). In Validation Cohort 1, FTLD-TDP cases had lower p-Tau181 levels than FTLD-Tau cases (mean 12.3 vs. 19.4 pg/mL, p=0.031, FIG. 2), and a trend of increased Fas levels and decreased IL-23 levels (p=0.158, p=0.152, FIG. 2). Levels of the other biomarkers did not differ between FTLD-TDP and FTLD-Tau. Decreased p-Tau181 levels alone had moderate performance as a biomarker for FTLD-TDP, with area under the curve (AUC) of 0.750 (C.I. 0.581-0.926) in the ROC curve analysis (FIG. 3A).

The ratio of p-Tau181 to t-Tau (p/t-Tau ratio) was analyzed to account for possible inter-individual differences in the relative Tau phosphorylation at threonine 181. FTLD-TDP cases had significantly lower p/t-Tau ratio than FTLD-Tau cases (FIG. 2, mean 0.27 vs. 0.47, p=0.005), with AUC of 0.804 (C.I. 0.625-0.983) in the ROC curve analysis (FIG. 3A).

As further validation, CSF levels of Fas, IL-23, p-Tau181, and t-Tau in Validation Cohort 2 were measured including subjects recruited from Emory (no overlap with Validation Cohort 1 from Emory) and Penn. Validation Cohort 2 included patients with FTLD-TDP (n=33), FTLD-Tau (n=20), as well as subjects with AD and elevated CSF ratio of t-Tau to Aβ1-42 (t-Tau/Aβ42>0.39, n=25) and normal cognition (22, including 13 with PN. Subjects were included with other central (AD) and peripheral (PN) neurological disorders to determine whether the observed p/t-Tau phenomenon is specific to FTLD-TDP or merely reflective of brain or peripheral nerve disease. In Validation Cohort 2, AD patients were older than FTLD-TDP and FTLD-Tau patients at time of symptom onset and time of CSF collection, but all groups were otherwise similar in age at onset, age and disease duration at CSF collection, gender, and education. CSF Fas and IL-23 levels no longer associated with FTLD-TDP in Validation Cohort 2. ROC curve analysis showed that p/t-Tau ratio <0.372 differentiates FTLD-TDP cases from all non-FTLD cases with 82% sensitivity and 82% specificity (AUC of 0.838, C.I. 0.752-0.925, FIG. 3A; AUC of 0.835 if AD cases were excluded, C.I. 0.739-0.931), and FTLD-TDP cases from FTLD-Tau with 82% sensitivity and 62% specificity (AUC of 0.731, C.I. 0.589-0.874).

Figure 3B:
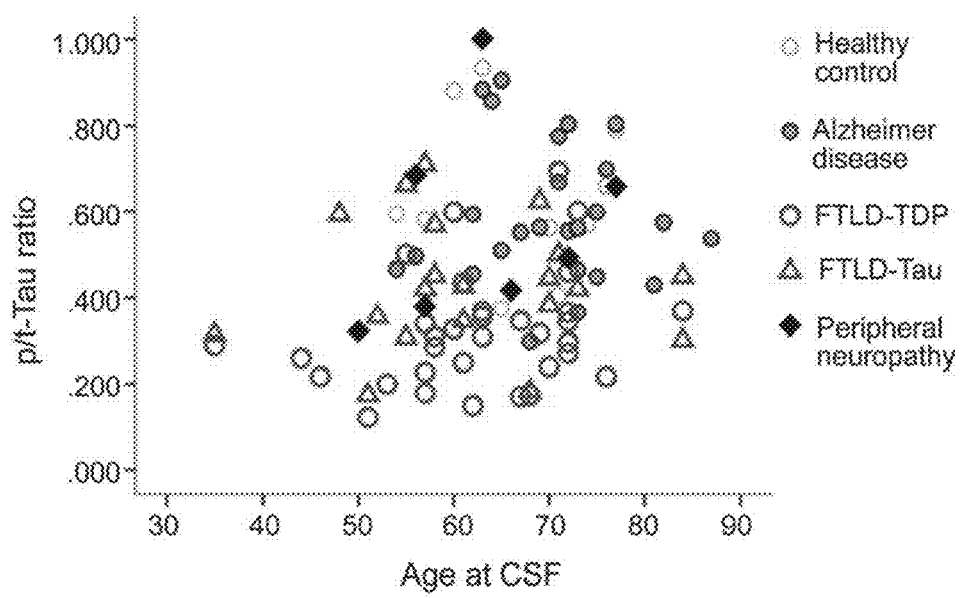
FIG. 3B shows data indicating analysis of both validation cohorts together showed no significant effect of age on the CSF p/t-Tau ratio.
Figure 3C:
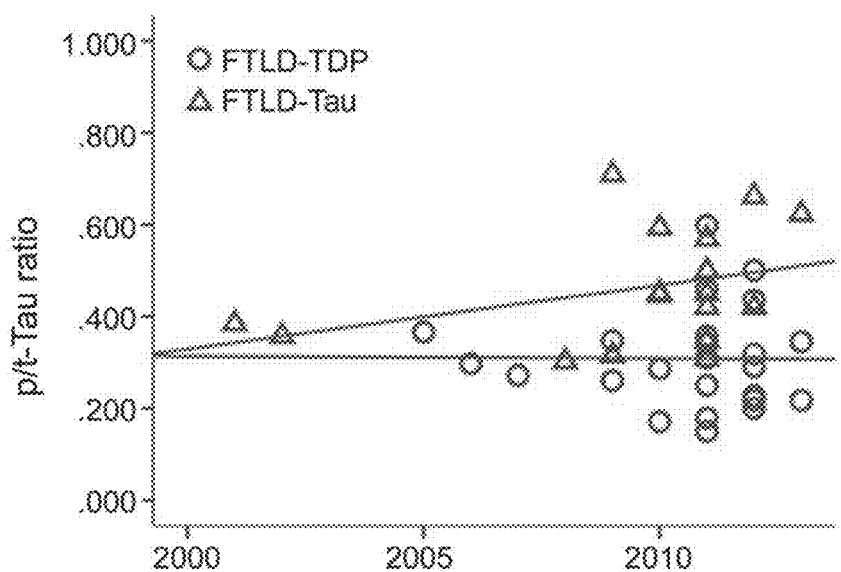
FIG. 3C shows data indicating CSF samples collected before 2009 had lower p/t-Tau ratio than CSF samples collected in or after 2009 in FTLD-Tau subjects (red line) but not FTLD-TDP subjects (blue line).
Figure 3D:
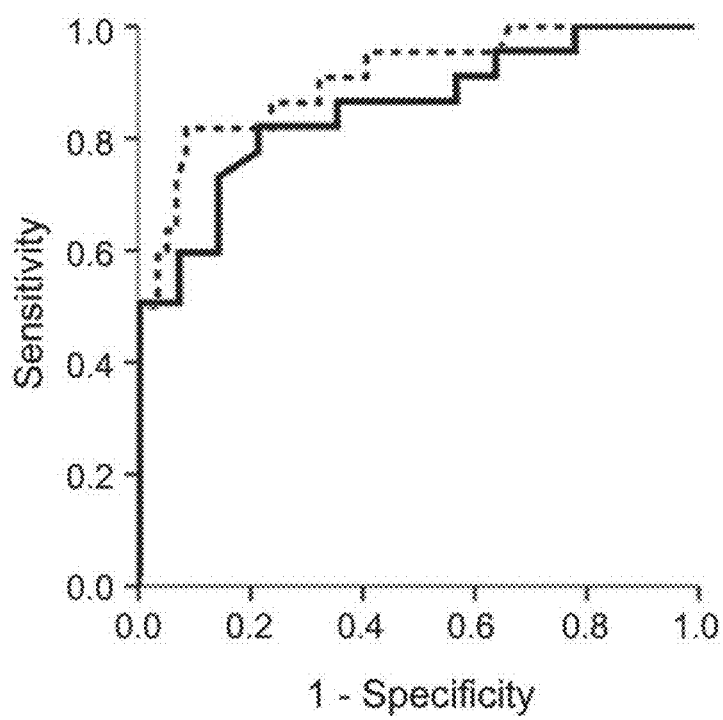
FIG. 3D shows data indicating when subjects whose CSF were collected before 2009 were excluded, the CSF p/t-Tau ratio remained an accurate biomarker to distinguish FTLD-TDP from FTLD-Tau (black solid line) or all non-TDP cases (black dashed line).

The observed performance in Validation Cohort 2 may be due to pre-analytical factors such as site of collection. Whether CSF p/t-Tau was influenced by center (Emory vs. Penn), age, gender, year of collection, and autopsy status was determined. This analysis revealed that decreased CSF p/t-Tau ratio in FTLD was not associated with the center of collection (p=0.607), age (FIG. 3B, p=0.391), gender (p=0.440), or autopsy status (p=0.193). However, while CSF p/t-Tau was stable in the FTLD-TDP cases regardless of number of years in −80° C. storage (p=0.257 in linear regression model), FTLD-Tau cases from before 2009 had lower CSF p/t-Tau levels than FTLD-Tau cases collected in 2009 or after (p=0.017, FIG. 3C). This was likely due to higher t-Tau levels in the pre-2009 FTLD-Tau cohort (71 pg/mL vs. 50 pg/mL, p=0.017 by Mann-Whitney U test). When only samples collected in 2009 or after were analyzed (FIG. 3D), CSF p/t-Tau ratio <0.37 was associated with a high diagnostic accuracy in distinguishing FTLD-TDP from FTLD-Tau cases only (ROC=0.849, C.I. 0.725-0.973) or all non-FTLD-TDP cases (ROC=0.908, C.I. 0.832-0.983).

As most autopsy-cases had longer freezer storage duration (n=25, mean 7.7 yr) than mutation (n=21, mean 1.85 yr) or clinical (n=37, mean 0.90 yr) cases, the difference in p/t-Tau ratio between FTLD-TDP and FTLD-Tau may be due to the inclusion of clinical cases. Therefore, whether CSF p/t-Tau ratio distinguished between FTLD-TDP and FTLD-Tau within each subgroup as autopsy and mutation confirmation are both criteria for definite FTLD were determined. Compared to FTLD-Tau cases, FTLD-TDP cases had lower CSF p/t-Tau ratio in both the mutation (n=0.046) and clinical (n<0.001) series, but only showed a trend of lower CSF p/t-Tau ratio in the autopsy (n=0.209) series.

The CSF p/t-Tau ratio is a reproducible biomarker for FTLD-TDP in a large number of FTLD patients recruited from two academic centers with known or high-confidence pathology. The performance of reduced CSF p/t-Tau ratio approximates that of the well-established CSF biomarker of t-Tau/Aβ42 for AD, although fluctuations after long-term freezer storage may limit its use in old samples. Assays for the two components of this ratio, p-Tau181 and t-Tau, are established in many neurodegenerative disease research centers, and international standardization effort is already underway given their importance in AD diagnosis and disease-modifying AD trials. Validation of reduced p/t-Tau ratio as an FTLD-TDP biomarker permits the rapid translation of this marker into current and future clinical trials for FTLD-TDP and FTLD-Tau.

The pathophysiological changes that result in a decreased p/t-Tau ratio in FTLD-TDP is unknown at this time. This is likely not due to increased p-Tau181 in FTLD-Tau as they had lower p-Tau181 levels and p/t-Tau ratio than healthy control subjects and AD cases. Alternatively, there may be altered Tau phosphorylation in the brain or CSF of FTLD-TDP patients which lead to the absence of hyperphosphorylated Tau in patients with FTLD due to the accumulation of pathologic FTLD-TDP. Immunoassays measured the absolute levels of t-Tau and p-Tau181 instead of global phosphorylation within each Tau peptide. Phosphorylation status at other Tau residues (e.g., p-Tau231) were not examined.

In the two single center cohorts (n=23 and n=30 in Validation Cohort 1), trends of higher Fas in FTLD-TDP were found. However, this association disappeared in the Validation Cohort 2 (n=53) at least in part due to the age-associated changes. Age is known to influence levels of CSF biomarkers such as Aβ1-4225 and α-synuclein, but its effect is only detectable with a sufficiently powered cohort. Age of the samples also altered CSF p/t-Tau ratio values and IL-23 levels. This effect from sample age reduced the ability of p/t-Tau to distinguish between autopsy-confirmed FTLD-TDP and FTLD-Tau with long freezer storage time, but p/t-Tau still distinguished between the two FTLD subtypes with pathogenic mutations fulfilling criteria of definite FTLD, confirming the notion that p/t-Tau reflects the FTLD pathology instead of clinical syndromes. Sample age is not a new pre-analytical factor, as four CSF analytes to undergo age (of the sample)-dependent changes in levels. Whether this is due to slow protein turnover, release from interacting proteins, or another mechanism is unclear.

CSF p/t-Tau ratio is a reproducible CSF biomarker to distinguish between FTLD-TDP and FTLD-Tau. The same ratio can be used to identify cases of ALS without cognitive impairment. ALS cases without dementia showed decreased CSF p/t-Tau compared to control subjects with p-Tau181 and t-Tau levels. While characterizing the clinical FTD syndromes remains important in symptomatic management and potentially tracking longitudinal progression, the use of a simple, accurate, and minimally-invasive biomarker can significantly enhance the design of therapeutic trials focused on abnormal inclusions containing TDP-43, or to exclude subjects with high likelihood FTLD-TDP from trials that target Tau pathology in FTLD-Tau patients. A tauopathy trial limited its enrollment only to patients with PSP due to the poor reliability of using clinical syndromes to predict FTLD-TDP or FTLD-Tau. With measures of CSF p/t-Tau ratio readily available in most laboratories involved in AD biomarker research, future clinical trials of drugs that target Tau or TDP can enrich their study population with patients with FTD syndromes and normal or low p/t-Tau ratio. In asymptomatic subjects from families with FTLD-TDP related mutations, a decrease in CSF p/t-Tau levels may herald early biochemical changes in the brain of these clinically normal subjects, similar to the early decrease in CSF A$\beta$42 levels in asymptomatic subjects with autosomal dominant AD mutations. CSF p/t-Tau can be used as a biomarker to identify subjects at very high risk of symptomatic FTLD-TDP for prevention trials similar to those on-going in familial AD.

CSF A$\beta$42 Solubility—Implications on CSF-Based Diagnosis of Alzheimer's Disease The clinical distinction between different neurodegenerative disorders can be challenging in patients with very mild neurological deficits. Recent diagnostic guidelines for AD have called for increased use of substrate-specific biomarkers for pre-clinical (asymptomatic) and mild cognitive impairment (MCI) stages of AD. CSF AD biomarkers, including $\beta$-amyloid 1-42 (A$\beta$42), total tau (T-tau), and tau phosphorylated at threonine 181 (p-Tau181) represent such biomarkers, and altered levels of these biomarkers highly associated with future conversion to dementia. Studies using ante-mortem CSF samples from subjects who were followed longitudinally to autopsy showed that CSF A$\beta$42 is sensitive for AD at the cost of specificity, CSF t-Tau is specific for AD but lacks sensitivity, and the ratio of CSF t-Tau to A$\beta$42 (t-Tau/A$\beta$42) appears to strike a balance between sensitivity and specificity. The reason for this balance is unknown. Data herein indicates that CSF A$\beta$42 measured using the Alzheimer's Disease Neuro-imaging Initiative (ADNI) protocol represents only a fraction of the total CSF A$\beta$42, and the measured proportion of total CSF A$\beta$42 is associated with CSF t-Tau and apolipoprotein J (apoJ) levels, two other proteins implicated in AD pathogenesis. Similarly, CSF t-Tau and p-Tau181 levels measured using the ADNI protocol are lower than the total CSF t-Tau and p-Tau181 levels. In vitro and in vivo factors which can influence the relative CSF A$\beta$42 solubility were determined, and cut-off values for diagnostic purposes based on pre-analytical procedures were derived.

A critical pre-analytical step is consistently associated with an approximately 1.5-2-fold difference in A$\beta$42 levels and 10-20% difference in t-Tau and p-Tau181 levels. The difference between total and soluble A$\beta$42 is strongly influenced by apoJ and t-Tau levels along with the standard freeze-thawing cycle common to most biomarker studies. This difference in measured A$\beta$42 levels gives rise to two distinct sets of cut-off values based on the population of AD biomarkers analyzed, and CSF A$\beta$42 solubility is a candidate biomarker for interventions involving enhanced levels of A$\beta$-interacting proteins.

Reproducible measurements of CSF AD biomarkers, especially A$\beta$42, have been a major challenge in their translation to clinical use. CSF A$\beta$42 levels measured by enzyme-linked immunoassays (ELISA) are generally in the range of 200-600 pg/mL, while CSF A$\beta$42 levels measured by Luminex assays are generally in the range of 50-250 pg/mL. This discrepancy was previously attributed to platform and antibody differences, but similarly discrepant results have been found in laboratories all using the same Luminex platform and assay kits (Les Shaw, private communication). As CSF AD biomarkers are known to be susceptible to pre-analytical factors such as diurnal variation and collection tube material, it is not surprising that pre-analytical protocol variations following lumbar puncture can result in significant variations in measured biomarker levels. The biggest discrepancy in A$\beta$42 level came from the standard freeze-thawing cycle universally applied to CSF biomarker work to prevent protein degradation, and the effect of decreased A$\beta$42 solubility was further amplified by measuring soluble instead of total A$\beta$42. The measured total CSF A$\beta$42 levels here are in the range of reported values from studies using ELISA. While these factors may not account for the large differences in t-tau and p-Tau181 levels between ELISA and Luminex platforms, establishing uniform pre-analytical procedures should significantly reduce the inter-lab variability in CSF A$\beta$42, t-Tau, and p-Tau181 measurements using the same assays.

Biological factors were identified at the individual level which can affect the measurement and diagnostic performance of CSF AD biomarkers. ApoJ and apoE, two well-characterized A$\beta$42 interacting proteins, each influences the difference between total and soluble A$\beta$42 with apoJ having a more dominant effect in the final model. ApoJ is known to bind A$\beta$42 in the CSF and can prevent A$\beta$ aggregation. Animal experiments have shown that knocking out apoJ reduces the soluble pool of brain A$\beta$ by approximately 50%. CSF apoJ level itself has been proposed as a biomarker for AD, but its complex relationship with A$\beta$ together with its intra- and extra-cellular localization makes apoJ level an unlikely stand-alone biomarker for AD diagnosis or prognosis. Nevertheless, because CSF apoJ is more accessible than interstitial or intracellular apoJ, CSF apoJ level should be added as an independent factor or interaction term to a model of MCI/AD prognosis. For example, even though apoJ level may not accurately predict current cognitive status or future cognitive decline, it may enhance a predictive model built on total A$\beta$42 levels as well as A$\beta$42 solubility to account for free and apoJ-bound A$\beta$42. With modulation of apoJ being considered as a future therapy for Alzheimer's disease and other amyloidoses, monitoring of distinct A$\beta$42 pools relative to apoJ levels sets the stage for future biomarker panels which can be used to stratify and monitor patients in such trials Along with the effects of apoE and apoJ levels on A$\beta$42 solubility, the biological significance of soluble A$\beta$42 (per ADNI protocol) remains to be elucidated. Soluble A$\beta$42 levels correlate with cerebral amyloid deposition, hippocampal atrophy, and longitudinal cognitive decline, but the strong correlation between soluble and total A$\beta$42 suggests that these associations will persist using only total A$\beta$42 levels (not influenced by apoJ or freeze-thawing). As typical pre-analytical processing exaggerates the insolubility of A$\beta$42 in a Tau level-dependent fashion, soluble A$\beta$42 as an AD biomarker may be best considered a dynamic biomarker rather than a static biomarker for AD. In other words, even though there was rare disagreement between total and soluble t-Tau/Aβ42 ratio in predicting underlying AD etiology at the dichotomous level, soluble t-Tau/Aβ42 ratio is a much more complex term than total t-Tau/Aβ42 as the denominator in the soluble ratio term is a function of total Aβ42, t-Tau, and apoJ. Hence, the numerical values of soluble Aβ42 and t-Tau/Aβ42 better predict continuous outcomes (rates of cognitive decline, correlation with cerebral amyloid imaging, response to amyloid immunotherapy) than biomarkers using total Aβ42.

EXPERIMENTAL

Reduced CSF p-Tau181 to Tau Ratio is a Biomarker for FTLD-TDP

Patients (23) from Emory University were included in the training set. All these patients had pathogenic FTLD mutations (n=5; 3 with C9ORF72 mutations, 1 with PGRN mutation, and 1 with MAPT mutation14) or an FTLD-plus disorder (n=18). An FTLD-plus disorder is defined as progressive behavior or language difficulties in the setting of a FTLD spectrum disorder invariably associated with FTLD-TDP or FTLD-Tau. These include amyotrophic lateral sclerosis (ALS) which is invariably associated with FTLD-TDP pathology with the exception of patients with mutation in the SOD1 gene, and progressive supranuclear palsy (PSP) which is highly associated with FTLD-Tau pathology. Patients were grouped according to their most likely underlying pathology, with the FTLD-TDP group (n=14) consisting of patients with associated mutations (C9ORF72, PGRN) and FTLD-ALS, and the FTLD-Tau group (n=9) consisting of patients with associated mutations (MAPT) and FTLD-PSP. None of the patients had elevated t-Tau/Aβ42 ratio greater than or equal to 0.30 (local cut-off according to modified protocol; see Methods) suggestive of underlying AD.

At the group level, FTLD-TDP cases had lower p-Tau181 levels and p-Tau181 to t-Tau ratios than FTLD-Tau cases (FIG. 1A). Receiver-operating characteristics (ROC) curve analysis showed sensitivity of 93% and specificity of 78% in detecting FTLD-TDP cases in the training cohort. If cases of corticobasal syndrome (n=2, likely FTLD-Tau) and semantic variant primary progressive aphasia (n=3, likely FTLD-TDP) were included in the analysis after eliminating cases with CSF Alzheimer's biomarker profiles, p-Tau181/t-Tau ratio ≤0.326 achieved sensitivity of 94% and specificity of 82% in identifying FTLD-TDP (FIG. 1B). Interestingly, instead of FTLD-Tau cases having higher p-Tau181/t-Tau ratio than non-FTLD-Tau cases, FTLD-TDP cases had significantly lower p-Tau181/t-Tau ratio than cases with FTLD-Tau, Alzheimer's disease, and normal cognition.

To validate these findings, an independent test cohort recruited from the University of Pennsylvania (Penn, FIG. 1A) including 11 with FTLD-TDP (0 with mutations and 11 with FTLD-ALS) and 8 with FTLD-Tau (0 with mutations and 8 with FTLD-PSP) were used. With a cut-off value of 0.326, p-Tau181/t-Tau ratio was able to identify FTLD-TDP cases with 82% sensitivity and 87.5% specificity.

TABLE 1

Baseline characteristics of the two validation cohorts.

| | Validation Cohort 1 | | Validation Cohort 2 | | | | |
|---|---|---|---|---|---|---|---|
| Diagnosis | FTLD-TDP (n = 19) | FTLD-Tau (n = 11) | FTLD-TDP (n = 33) | FTLD-Tau (n = 20) | AD (n = 25) | Healthy Control (n = 13) | Peripheral Neuropathy (n = 9) |
| Male, n (%) | 14 (74%) | 8 (73%) | 13 (42%) | 11 (55%) | 11 (44%) | 5 (38%) | 4 (44%) |
| Education, yr (SD) | 15.·0 (2.2) | 14.3 (2.5) | 15.2 (3.0) | 14.0 (3.3) | 15.9 (2.8) | 16.5 (2.7) | 14.1 (1.9) |
| FTLD subgroups | 4 autopsy 4 mutation 7 FTD-ALS 4 SemD | 5 autopsy 1 mutation 5 FTD-PSP | 11 autopsy 10 mutation 9 FTD-ALS 3 SemD | 5 autopsy 6 mutation 9 FTD-PSP | | | |
| Age at onset, yr (SD) | 65.2 (8.4) | 60.8 (10.7) | 59.7 (9.5) | 58.1 (11.1) | 66.2 (7·7) | — | 59.7 (9.5) |
| Age at CSF, yr (SD) | 68.9 (8·3) | 64·9 (10.1) | 62.7 (10.1) | 61.8 (11.9) | 70.1† (7.8) | 66.2 (8.0) | 63·0 (9.5) |
| Disease duration, yr (SD) | 3.7 (3.2) | 4.0 (2.2) | 2.9 (1.9) | 3.3 (2.4) | 3.1 (2.4) | — | 3.3 (3.1) |
| p-Tau$_{181}$, pg/mL (SD) | 12.6 (6.9) | 22.0 (13.5) | 15.7 (6.9) | 20.3 (7.0) | 66.2‡ (45.1) | 35.5 (18.3) | 26.0 (5.6) |
| t-Tau, pg/mL (SD) | 65.5* (36.6) | 58.3 (29.0) | 53.2 (22.1) | 52.3 (23.4) | 116.4‡ (72.0) | 49.2 (24.4) | 45.5 (0.70) |
| p-Tau$_{181}$/ t-Tau (SD) | 0.267** (0.110) | 0.468 (0.215) | 0.311¶ (0.127) | 0.446 (0.137) | 0.594 (0.164) | 0.646 (0.201) | 0.505 (0.237) |

Values shown for continuous variables are mean with standard deviations in parentheses.
*p = 0.017 compared to FTLD-Tau;
**p = 0.002 compared to FTLD Tau;
†older than FTLD-TDP (p = 0.038) Tau (p = 0.042);
‡higher than healthy control (p < 0.002), FTLD-TDP (p < 0.001), FTLD-Tau (p < 0.001), and peripheral neuropathy (p < 0.06);
¶lower than healthy control (p < 0.001), AD (p < 0.001), FTLD-Tau (p = 0.04), and peripheral neuropathy (0.017).
AD: Alzheimer's disease;
SemD = Semantic dementia with CSF not consistent with AD.

Standard Protocol Approvals, Registrations, and Patient Consents

Studies conducted at Emory were approved by the Emory Institutional Review Board, and studies conducted at Penn were approved by the Penn Institutional Review Board. Informed consents were obtained from each subject or his/her legal representative.

Subjects

Volunteers were prospectively recruited to undergo antemortem CSF collection (FIG. 1). Emory samples included those prospectively collected from 2010 to 2013, and Penn samples included samples collected from 1997 to 2013. Because the exact FTLD pathology is unknown in most clinically diagnosed patients, patients were included and followed to autopsy with neuropathologically-confirmed diagnosis of FTLD-TDP or FTLD-Tau (n=25), and patients carrying mutations predictive of FTLD-TDP (C9ORF72 and PGRN, n=14) or FTLD-Tau (MAPT, n=7). Genetic testing for mutations in C9ORF72, PGRN, and MAPT were performed at Penn for Penn samples, and at Athena Diagnostics (Worchester, Mass.) or at Penn for Emory samples. The cohorts were enriched with subjects with FTD-Plus syndromes in which the additional clinical diagnosis accurately predicts the pathology, including FTD-ALS (with ALS characterized by inclusions immunoreactive to TDP-43, n=16) and FTD-PSP (with PSP characterized by inclusions immunoreactive to Tau, n=14). Finally, patients with semantic dementia (SemD) and normal CSF Tau and beta amyloid 1-42 (Aβ42) levels (i.e., inconsistent with a diagnosis of AD), a primary progressive aphasia syndrome highly associated with FTLD-TDP after exclusion of AD cases, 12 were also included (n=7). Consecutive patients were recruited if they fulfill the inclusion criteria. Each patient underwent detailed neurological and laboratory examination to ensure the accuracy of clinical diagnosis according to established criteria for AD, bv-FTD, SemD, FTD-ALS, and FTD-PSP. Subjects with ALS only or PSP only were not included, as discovery work using populations preferentially biased towards these two groups may reveal CSF changes associated with the particular disease rather than the general FTLD pathologic subtype. In addition, subjects were recruited with AD, normal cognition with and without peripheral neuropathy (PN) from Emory for this study to determine whether biomarker changes were specific to FTLD-TDP or non-specifically associated with brain or peripheral nerve disease. Apolipoprotein E (APOE) genotyping was performed at each center.

CSF Sampling and Analysis

Baseline CSF samples were obtained prospectively before measurement of CSF biomarkers according to protocols similar to the AD Neuroimaging Initiative (ADNI). Lumbar puncture was performed with a 20- or 24-guage spinal needle, and CSF was collected into polypropylene tubes. Aliquots (0.5 mL) were immediately prepared, bar-coded, frozen and stored at −80° C. until analysis. Samples from Penn were shipped overnight on dry ice to Emory and handled in a manner that avoids changes in pH due exposure of frozen samples to CO2 and carbonic acid. No complications from lumbar punctures were observed in the current study.

CSF levels of all biomarkers were measured at Emory. CSF levels of Aβ42, t-Tau, and p-Tau181 were measured with commercially available kits (AlzBio3, Innogenetics, Ghent, Belgium) in a Luminex 200 platform by a single experienced technician (KW) blinded to the FTLD grouping. Specifically, frozen aliquots were allowed to thaw at room temperature for 30 min, and each aliquot was then vortexed vigorously for 15 sec. Once the necessary reagents were loaded into the assay plate, each aliquot was then re-vortexed for 15 sec immediately before being loaded into the corresponding wells. CSF AD-related peptides become more insoluble with time in vitro, resulting in variable loss of measured levels if vortexing immediately before well loading was omitted (ranging from 10-20% in t-Tau and p-Tau181 to nearly 50% for Aβ42). Because the reduction is not uniform for t-Tau and p-Tau181 within the same individual, the choice of total vs. soluble t-Tau and p-Tau181 can result in significant differences when the p/t-Tau ratio is calculated. The ratio of p-tau181 to t-Tau was calculated by dividing total p-Tau181 by total t-Tau.

Levels of other candidate CSF FTLD-TDP biomarkers were measured by modifying commercially available immunoassays. Agouti-related peptides (AgRP) and adrenocorticotropic hormones (ACTH) were measured in a multiplex assay (Millipore, Billerica, Mass.; 75 µL CSF, overnight primary antibody incubation at 4° C.), while eotaxin-3 (Millipore, Billerica, Mass.; 200 µL CSF, overnight primary antibody incubation at 4° C.), Fas (Affymetrix/Procarta, Santa Clara, Calif.; 100 µL CSF, 1 hr primary antibody incubation at room temperature), and interleukin-23 (IL-23, R&D Systems, Minneapolis, Minn.; 200 µL, 2 hr primary antibody incubation at room temperature) were measured in singleplex assays. Interleukin-17 (IL-17) measurements were tried in five commercial available kits (Millipore, Billerica, Mass.; Life Technologies, Grand Island, N.Y.; Affymetrix/Procarta, Santa Clara, Calif.; R&D Systems, Minneapolis, Minn.; Affymetrix/eBioscience, San Diego, Calif.) with no reliably detectable levels. IL-17 in the original biomarker panel was thus replaced by IL-23 as IL-23 is an upstream effector of IL-17 and CSF IL-23 levels were significantly decreased in FTLD-TDP compared to FTLD-Tau.

Effects of Pre-Analytical Factors on Analyte Levels

Pre-analytical factors may influence CSF analyte levels, including age, gender, duration of freezer storage, and freeze-thawing cycles. The effects of age, gender, and storage duration were assessed statistically (see below). Freeze-thawing effects were determined empirically by having CSF samples from five randomly chosen subjects undergo up to three freeze-thaw cycles.

Statistical Analysis

Statistical analysis was performed in IBM SPSS 20 (Chicago, Ill.). Chi-squared test, and Student's T-test (for two subgroups) or analysis of variance (for three or more subgroups) were used to detect uni-variate differences between subgroups. Mann-Whitney U-tests were used to determine if levels of AgRP, ACTH, eotaxin-3, Fas, IL-23, t-Tau, and p-Tau181 differed between FTLD-TDP and FTLD-Tau in the first validation cohort. Receiver operating characteristics (ROC) curve analysis was used to determine the area under the curve (AUC) including 95% confidence interval (C.I.) values, as and cut-off points were chosen to achieve sensitivity and specificity greater than 80%. Data from the Validation Cohort 1 (Emory) was used to calculate the necessary sample size in the two-centered Validation Cohort 2 (Emory and Penn, with no overlap between the two validation cohorts) using G*Power 3.1.5 (Kiel, Germany). With a calculated effect size of 0.93 from Validation Cohort 1 for p/t-Tau, a sample size of 28 FTLD-TDP and 18 FTLD-Tau has power of 0.90 in detecting a difference in CSF p/t-Tau between the two groups at α=0.05. In Validation Cohort 2, ROC curve analysis was performed with and without the inclusion of AD subjects with increased t-Tau/

Aβ42 ratio to determine if the overall predictive accuracy can be improved by incorporating CSF AD biomarkers into the diagnostic algorithm.

To determine the effects of pre-analytical factors, Mann-Whitney U-test was used to compare the distribution of p/t-Tau ratio between categorical factors (gender, presence of APOE ε4 allele, autopsy status), and linear regression analysis was used to determine the effects of age and collection year.

Soluble CSF Aβ42 Represents Half of Total CSF Aβ42

Figure 4A:
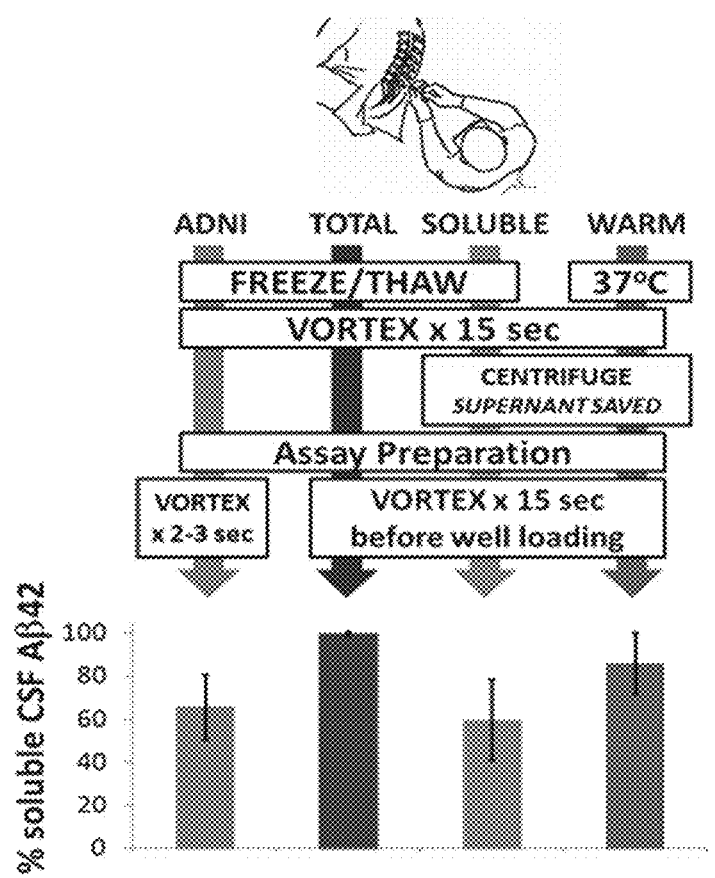
FIG. 4A shows data indicating CSF Aβ42 solubility is influenced by pre-analytical processing as well as disease status. Four distinct pre-analytical protocols lead to differences in measured CSF Aβ42 levels. All values are represented as percent of biomarker levels measured per Total protocol to account for inter-individual differences in biomarker levels. "ADNI" is the standard protocol involving no centrifugation and limited vortexing immediately prior to plate loading. "Total" represents total measurable CSF Aβ42 per Emory protocol with vigorous vortexing immediately prior to plate loading. "Soluble" represents the soluble fraction of CSF Aβ42 per Emory protocol, and is generated by centrifuging the CSF sample for 15 min and removing the top 200 μL. "Warm" represents a variation of the "soluble" fraction, except CSF aliquots are kept at 37° C. immediately after collection and immediately analyzed for biomarker levels within 2 hr.
Figure 4B:
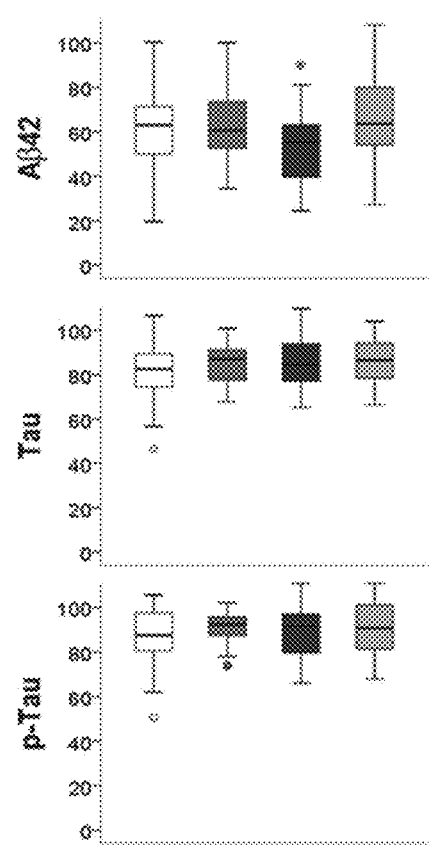
FIG. 4B shows comparisons of the soluble fractions of AD biomarkers according to diagnosis (normal cognition; mild cognitive impairment; Alzheimer's disease; other non-AD dementia).
Figure 5:
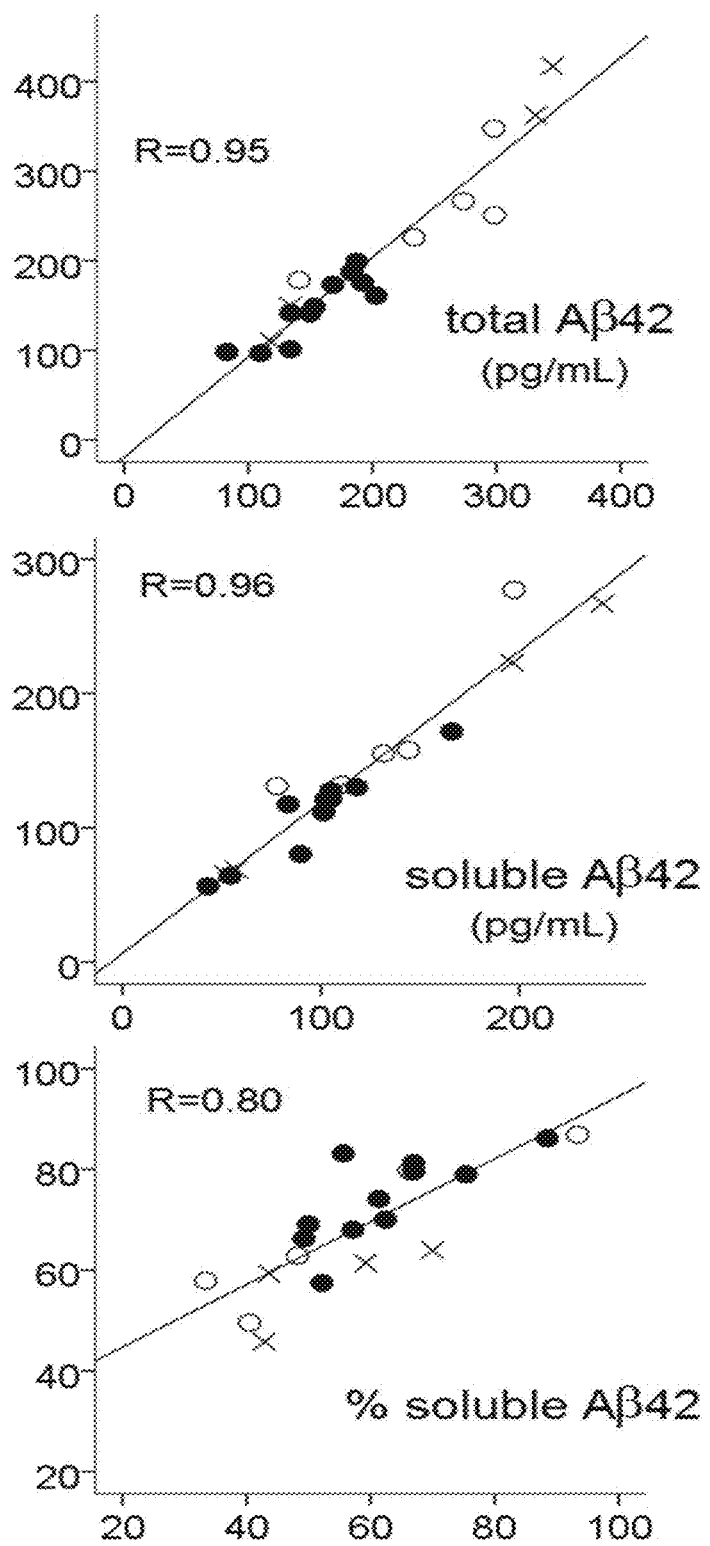
FIG. 5 shows data on the correlation of CSF Aβ42 levels in 20 duplicate samples measured independently by two independent laboratories. Levels measured at Emory University are shown on the X-axis, while levels measured at University of Pennsylvania are shown on the Y-axis (Open circles: normal cognition; filled circles: MCI and AD; crosses: non-AD dementia).

CSF AD biomarker levels were measured in two adjacent CSF aliquots processed according to the ADNI protocol or the Emory protocol. Soluble (Emory protocol) and ADNI Aβ42 levels were indistinguishable from each other, but both were significantly lower than total Aβ42 levels processed by the Emory protocol (FIG. 4a). Using the entire cohort of subjects (n=140), soluble Aβ42 levels were significantly lower than total Aβ42 levels (p<0.001), and on average represented 57.0% of total Aβ42 levels (S.D.=16.6%). Soluble CSF Aβ42 levels correlated strongly with total Aβ42 levels (R=0.818, p<0.001). When stratified by clinical diagnosis, subjects with clinical AD had lower CSF Aβ42 solubility than subjects with normal cognition, MCI, or non-AD dementia (FIG. 4b). Paired T-tests also showed soluble t-Tau and p-Tau181 levels to be lower than total t-Tau and p-Tau181 levels (FIG. 4c), but the difference in levels (15.3%±16.5% for t-Tau, 12.4%±20.9% for p-Tau181) is smaller than that seen for Aβ42.

Reproducibility of Soluble and Total CSF AD Biomarkers

To replicate findings of two separate pools of CSF Aβ42, never thawed CSF aliquots from 20 identical subjects were shipped to Penn for AD biomarker measurements using the Emory protocol. These included 5 healthy subjects, 5 subjects with MCI, 6 subjects with AD, and 4 subjects with non-AD disorders. Soluble and total CSF Aβ42 values levels correlated strongly between Emory and Penn (R=0.846 and 0.774, FIG. 2), as well as the ratio of soluble to total Aβ42 (% soluble Aβ42, R=0.841).

Cut-Off Values for Soluble Vs. Total t-Tau/Aβ42

As soluble Aβ42 levels represent approximately half of total Aβ42 levels, the use of soluble or total Aβ42 level in the diagnostic algorithm for AD can significantly impact the performance of a universal cut-off value for Aβ42 and t-Tau/Aβ42. The corresponding cut-off values using total Aβ42 and t-Tau/Aβ42 were examined based on previously published values. Soluble Aβ42 level cut-off of 192 pg/mL corresponds to total Aβ42 level of 310 pg/mL, with subjects having concordant Aβ42 status (normal vs. decreased) in 121/140 cases (86.4%). Compared to subjects who have concordant Aβ42 status, those predicted to have AD-like CSF by soluble but not total Aβ42 (n=13) had lower Aβ42 solubility (42.3% vs. 57.5%, p<0.001), and those predicted to have AD-like CSF by total but not soluble Aβ42 (n=6) had higher Aβ42 solubility (78.0% vs. 57.5%, p<0.001). On the other hand, soluble t-Tau/Aβ42 ratio cut-off of 0.39 corresponds to total t-Tau/Aβ42 ratio of 0.28, with higher concordance rate between the two ratio markers (136/140 cases, or 97.1%).

Effect of a Single Freeze-Thaw Cycle on CSF Aβ42 Solubility

Most biomarker protocols involve immediate freezing at −80° C. until analysis. As protein solubility can be influenced by temperature, we first tested if a single freeze-thaw cycle would alter Aβ42 solubility. Compared to CSF handled through the typical fashion, keeping the CSF samples at 37° C. for up to 2 hours between collection and analysis without freeze-thawing resulted in much higher solubility (mean 82.7%, S.D. 14.5%, p=0.028 by Mann Whitney U-test, FIG. 1c). Thus, the standard freezing step involved in long-term storage likely lowered in vivo CSF Aβ42 solubility, and the measured in vitro soluble CSF Aβ42 levels may be significantly lower than the physiological soluble CSF Aβ42 levels.

Relationship Between Aβ42 Solubility and Other CSF Protein Levels

Other than temperature, solubility of the hydrophobic Aβ42 can be altered by binding proteins. To determine which candidate CSF proteins influence Aβ42 solubility, whether soluble CSF Aβ42 levels were influenced by levels of other proteins implicated in AD (apoE, apoJ, albumin, α-synuclein) was determined in a cohort (n=69). Linear multi-variate regression analysis showed that while total CSF Aβ42 levels were only correlated with MCI or AD diagnosis, soluble CSF Aβ42 levels were influenced by levels of apoJ and t-Tau as well as age and the presence of APOE ε4 allele (Table 2). Similarly, CSF Aβ42 solubility is most associated with apoJ (F=26.5, p<0.001) and t-Tau (F=16.0, p<0.001) levels, even when age, gender, diagnosis, disease duration, and CSF biomarker (Aβ42, p-Tau181, apoE, albumin, α-synuclein) levels were entered into the model.

Figure 6A:
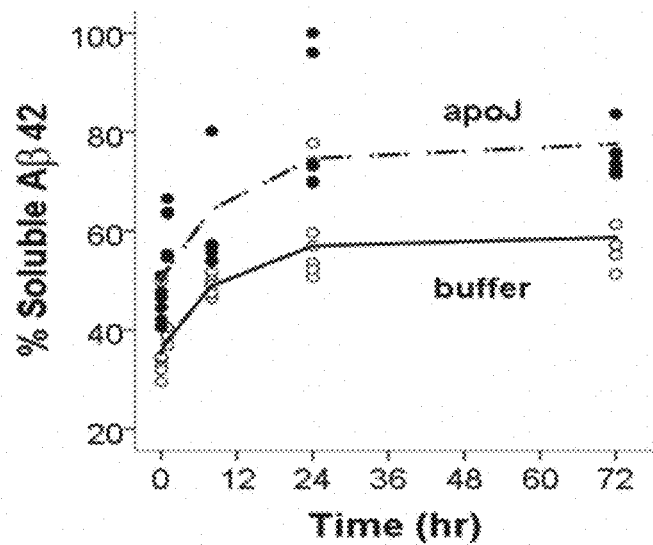
FIG. 6A shows data on factors which influence relative CSF Aβ42 solubility. Incubation of CSF at 37° C. gradually increases the in vitro CSF Aβ42 solubility until it reaches a plateau at 24-72 hours, and incubation of CSF at 37° C. with additional apoJ increases the asymtotic plateau in a parallel time-dependent fashion.
Figure 6B:
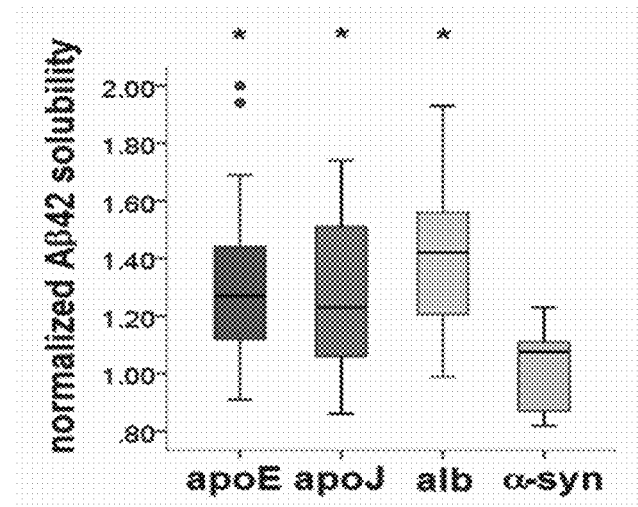
FIG. 6B shows data indicating the addition of exogenous apoE, apoJ, and albumin, but not α-synuclein or cystatin C, increases the in vitro CSF Aβ42 solubility. Solubility was determined after 4 hr of incubation at 37° C.

Whether increased apoJ levels merely accelerate the return of in vitro Aβ42 solubility from its in vivo levels, or enhance the overall Aβ42 solubility was determined. Five subjects we selected with low CSF Aβ42 solubility by design to avoid the ceiling effect on solubility. Incubating CSF samples which have gone through one freeze-thaw cycle at 37° C. gradually increased Aβ42 solubility following an asymptotic curve over 72 hours. When purified apoJ was added at baseline, Aβ42 solubility increased asymptotically over the same period, but to a significantly higher final level (FIG. 6a). Addition of purified apoE and albumin also increased the CSF Aβ42 solubility after 4 hrs (p=0.029, and p<0.001, FIG. 6b), but addition of purified α-synuclein and cystatin C did not.

Participants

Patients and control subjects were recruited and longitudinally followed in the Emory Clinic or the Emory Alzheimer's Disease Research Center (ADRC). The study was approved by the Emory University Institutional Review Board, and informed consent was obtained from all patients or their authorized representatives. Participants (n=140) included community-dwelling healthy volunteers with normal cognition and cognitively impaired patients evaluated at subspecialty clinics dedicated to the evaluation of neurodegenerative disorders including mild cognitive impairment (MCI), AD, frontotemporal dementia (FTD) and related disorders (including amyotrophic lateral sclerosis (ALS) with and without dementia, corticobasal syndrome and progressive supranuclear palsy with and without dementia), and dementia with Lewy bodies (DLB). APOE genotyping was performed on all but four participants in the current study.

Procedures

Samples were collected from subjects according to strict protocols. At sample collection, participants were ≥21 years of age and in good general health, having no other psychiatric or major medical diagnoses that could contribute significantly to cognitive impairment or dementia other than the primary neurodegenerative disorder. CSF samples were collected between 8 AM and 2 PM without overnight fasting based on the ADNI protocol. Specifically, a 24-guage Sprotte spinal needle is inserted into the L3-4 or L4-5 interspace, and 15 mL of CSF was collected into two 10 mL polypropylene syringes and then transferred into a 15 mL polypropylene tube (BD Falcon). The spinal fluid is inverted 2-3 times, and immediately divided into pre-labeled 500 μL aliquots. When appropriate, aliquots were sent for clinical laboratory testing. The remaining aliquots were immediately frozen and stored at −80° C. until analysis.

On day of analysis, CSF aliquots are allowed to thaw at room temperature for 30 minutes. CSF samples were then processed according to two different protocols (FIG. 3a):

1) ADNI protocol: All aliquots are sequentially vortexed for 10 seconds each until all samples have been vortexed. Immediately before well-loading, each aliquot is re-vortexed for 2 seconds.

2) Emory Protocol: Each 500 μL aliquot of CSF is vortexed vigorously for 15 seconds before being divided into two 250 μL aliquots with one portion labeled "total". The other 250 μL aliquot is centrifuged at 15000 rpm for 15 minutes in a tabletop centrifuge, and the top 200 μL of CSF is removed and labeled as "soluble". This portion is not a supernatant as no pellet was visible using light microscopy. Immediately before well-loading, each aliquot is re-vortexed for 15 seconds.

To determine the effect of the single freeze-thaw cycle after CSF collection, nine CSF samples were processed according to the Emory Protocol with the exception that CSF aliquots were kept at 37° C. in water bath and analyzed immediately within 2 hours (FIG. 3a). CSF levels of AD biomarkers (Aβ42, total tau, and p-tau181) were measured using the multiplex xMAP Luminex platform (Luminex Corp, Austin, Tex.) with AlzBio3 kits (Innogenetics, Ghent, Belgium) according to manufacturer's protocol. CSF Aβ42 solubility was determined as the ratio of soluble to total CSF Aβ42.

Replication of Distinct CSF Aβ42 Pools

Duplicate aliquots of CSF from 20 subjects were sent to University of Pennsylvania on dry ice overnight, and CSF was processed according to Emory protocol to derive total and soluble CSF Aβ42 levels. CSF Aβ42 solubility was independently measured and then compared with values measured at Emory.

Other CSF Proteins that Influence CSF Aβ42 Solubility

Aβ42 is known to interact with other proteins including apoJ, apolipoprotein E (apoE), and α-synuclein. To determine whether CSF Aβ42 solubility is influenced by these interacting proteins, we measured their levels in a smaller cohort of 69 subjects chosen from the larger cohort. This subcohort was randomly selected and were similar to the unselected subjects in terms of age, gender, disease duration, and CSF AD biomarker levels. CSF apoE levels were measured at 1:25 dilution (Millipore, Billerica, Mass.; CSF diluted 1:25); apoJ levels were measured at 1:500 dilution (Millipore, Billerica, Mass.); α-synuclein (Invitrogen, Camarillo, Calif.) and total protein levels (Pierce, Rockford, Ill.) were measured at 1:1 dilution. Levels of these interacting proteins were then entered into a multi-variate linear regression model to determine the strongest factors predicting CSF Aβ42 solubility.

Furthermore, whether increasing levels of these Aβ42-interacting proteins would alter CSF Aβ42 solubility was analyzed. As apoJ strongly predict Aβ42 solubility, the time-dependent effect of increasing apoJ levels was determined. Five CSF aliquots were selected from five patients with low Aβ42 solubility. Lyophilized purified apoJ (BioVendor, Candler, N.C.) was resuspended in and apoJ or buffer was added to each subject's CSF aliquots. In the apoJ samples, the final concentration was 16,000 ng/mL (3 times the average apoJ concentrations). Paired buffer-apoJ treated CSF aliquots were incubated at 37° C. for 0, 1, 8, 24, and 72 hrs to construct the temporal profiles of Aβ42 solubility. Asymptotic curve fitting was performed to visualize the overall effects of time and apoJ on Aβ42 solubility, and repeated measures analysis was used to assess the significance of apoJ addition. All solubility values were determined by dividing time- and treatment-dependent soluble Aβ42 levels by baseline, buffer-treated total Aβ42 levels. After evaluation of the time course, the effects of increasing apoJ, apoE (Millipore, Billerica, Mass.), albumin (Jackson ImmunoResearch Laboratories, West Grove, Pa.), and α-synuclein (rPeptide, Bogart, Ga.) were compared to Aβ42 solubility after 4 hours of incubation at 37° C. in subjects with wider ranges of Aβ42 solubility. ApoE, albumin, and α-synuclein concentrations were 10.4 μg/mL, 401 μg/mL, and 1.20 ng/mL. To account for baseline differences in Aβ42 solubility, treatment-dependent Aβ solubility was determined first by dividing the final soluble Aβ42 levels by total Aβ42 levels at baseline, and then normalized to baseline buffer-treated Aβ42 solubility.

TABLE 2

Baseline demographic and biomarker features of the Emory cohort.

|  | Normal Cognition (n = 30) | MCI (n = 36) | AD (n = 36) | Other dementia (FTD, LBD, NPH; n = 38) | p |
|---|---|---|---|---|---|
| Age at CSF, yr (SD) | 66.9 (20.2) | 67.6 (8.1) | 64.7 (8.8) | 66.7 (7.8) | 0.760 |
| Male gender (%) | 12 (40%) | 25 (69%) | 16 (44%) | 25 (66%) | 0.027 |
| Disease duration, yr (SD) | N.A. | 2.6 (2.1) | 3.7 (1.9) | 3.5 (2.4) | 0.063 |
| Presence of APOE_4 allele (%) | 12 (40%) | 20 (55%) | 20 (56%) | 13 (34%) | 0.124 |
| CSF biomarkers |  |  |  |  |  |
| Total Ab42 | 325.5 (89.2) | 254.3 | 207.6 (77.4) | 286.4 (96.5) | <0.001** |
| Soluble Ab42 | 197.1 (86.5) | (114.9) | 105.6 (44.4) | 177.8 (86.2) | <0.001** |
| Total t-Tau | 54.2 (24.9) | 156.2 (92.1) | 120.0 (72.1) | 71.1 (37.6) | <0.001* |
| Soluble t-Tau | 45.7 (27.2) | 83.6 (44.1) | 102.8 (65.8) | 63.5 (32.6) | <0.001** |
| Total p-Tau$_{181}$ | 28.8 (16.2) | 72.3 (38.9) | 62.9 (39.3) | 27.2 (13.5) | <0.001* |
| Soluble p-Tau$_{181}$ | 25.5 (15.4) | 42.4 (20.5) 38.7 (19.3) | 55.3 (37.6) | 26.9 (12.7) | <0.001* |

TABLE 2-continued

Baseline demographic and biomarker features of the Emory cohort.

| | Normal Cognition (n = 30) | MCI (n = 36) | AD (n = 36) | Other dementia (FTD, LBD, NPH; n = 38) | p |
|---|---|---|---|---|---|
| Biomarker ratio | | | | | |
| Total t-Tau/Ab42 | 0.180 (0.096) | 0.412 (0.365) | 0.628 (0.359) | 0.288 (0.220) | <0.001** |
| Soluble t-Tau/Ab42 | 0.250 (0.145) | 0.641 (0.516) | 1.066 (0.593) | 0.462 (0.369) | <0.001* |
| # with multi-analyte profiling (%) | 14 (47%) | 20 (56%) | 20 (56%) | 15 (39%) | 0.123 |

*Subjects with AD and MCI differ from subjects with normal cognition or other dementia;
**subjects with AD differ from non-AD subjects (AD: Alzheimer's disease; MCI: mild cognitive impairment; FTD: frontotemporal dementia; LBD: Lewy body disease; NPH: normal pressure hydrocephalus).

TABLE 3

Biological factors which influence CSF Aβ42 solubility.

| Factors | B (95% confidence interval) | p |
|---|---|---|
| Total Aβ42 (pg/mL) | 0.625 (0.546, 0.705) | <0.001 |
| apoJ (pg/mL) | $1.34 \times 10^{-6}$ ($0.82 \times 10^{-6}$, $1.86 \times 10^{-6}$) | <0.001 |
| t-Tau (pg/mL) | −0.155 (−0.306, −0.005) | 0.043 |
| Constant | −76.55 (−10931, −43.79) | <0.001 |

In this model, soluble CSF Aβ42 levels were entered as the dependent variable, while age, gender, disease duration, presence of APOE4 allele, and biomarker levels (including total Aβ42, total t-Tau, total p-Tau$_{181}$, apoE, apoJ, albumin, and α-synuclein) were entered in a stepwise fashion. The final model had a $R^2$ of 0.841 in predicting soluble CSF Aβ42 levels.

I claim:

1. A method of diagnosing a frontotemporal lobar degeneration subtype comprising measuring total Tau and Tau phosphorylated at threonine 181 in a cerebrospinal fluid sample from a subject, calculating the ratio of Tau phosphorylated at threonine 181 to total Tau, recording the calculated ratio, and making a diagnosis of the subtype based on the calculated ratio,
    wherein the frontotemporal lobar degeneration subtypes are selected from frontotemporal lobar degeneration with immunoreactive lesions to Tau and frontotemporal lobar degeneration with immunoreactive lesions to TAR DNA binding protein of 43 kD, and
    wherein the cerebrospinal fluid is vortexed for 15 seconds immediately before measuring total Tau and Tau phosphorylated at threonine 181.

2. The method of claim 1, further comprising the step of measuring beta-amyloid 1-42, calculating the ratio of total Tau to beta-amyloid 1-42, and making a diagnosis of Alzheimer's disease or a frontotemporal lobar degeneration subtype.

3. The method of claim 1, wherein the measurements or ratio are recorded in an electronic format.

4. The methods of claim 1, further comprising the step of reporting the measurements, ratio, or diagnosis to a medical professional, the subject, or representative thereof.

5. The methods of claim 1, wherein a decrease relative phosphorylation of Tau at threonine 181 when compared to levels typical of a subject of normal cognition indicates frontotemporal lobar degeneration subtype with immunoreactive lesions to TAR DNA binding protein of 43 kD.

6. The methods of claim 1, wherein a phosphorylation of Tau at threonine 181 to total Tau ratio of less than about 0.3 indicates the subject has frontotemporal lobar degeneration subtype with immunoreactive lesions to TAR DNA binding protein of 43 kD.

7. The methods of claim 1, wherein a phosphorylation of Tau at threonine 181 to total Tau ratio of greater than about 0.3 indicates the subject has frontotemporal lobar degeneration with immunoreactive lesions to Tau.

8. The methods of claim 1, wherein the subject exhibits symptoms of progressive behavior or language difficulties.

9. The method of claim 1, further comprising the step of recording the diagnosis.

10. The method of claim 9, wherein the diagnosis is recorded in an electronic format.

* * * * *